United States Patent [19]

Lowder et al.

[11] Patent Number: 5,211,560

[45] Date of Patent: May 18, 1993

[54] ROTARY DENTAL ABRASIVE POLISHING APPLICATOR

[75] Inventors: James T. Lowder; Mark E. Watkins, both of Columbus, Ohio

[73] Assignee: Abrasive Technology, Inc., Westerville, Ohio

[21] Appl. No.: 625,751

[22] Filed: Dec. 11, 1990

[51] Int. Cl.$^5$ .............................. A61C 3/06
[52] U.S. Cl. .................... 433/166; 433/142
[58] Field of Search ............ 433/165, 166, 141, 142, 433/216

[56] References Cited

U.S. PATENT DOCUMENTS

| | | | |
|---|---|---|---|
| 3,964,166 | 6/1976 | Stahlman | 433/166 |
| 3,972,161 | 8/1976 | Zoiss | 51/206 R |
| 3,977,084 | 8/1976 | Sloan | 433/166 |
| 4,185,388 | 1/1990 | Jarby | 433/125 |
| 4,613,307 | 9/1986 | Neumeyer | 433/166 |
| 4,636,171 | 1/1987 | Martin | 433/134 |
| 4,984,985 | 1/1991 | Edwardson | 433/123 |

Primary Examiner—Gene Mancene
Assistant Examiner—Cindy A. Cherichetti
Attorney, Agent, or Firm—Francis T. Kremblas, Jr.

[57] ABSTRACT

A dental polishing applicator for use with a rotary dental handpiece and method of using the same which is characterized by a collet portion and a removably mounted, disposable single use tip portion. The cylindrical collet is adapted to be removably mounted to conventional dental handpieces and includes an opposing end adapted to removably receive a shaft portion of the applicator tip portion. Preferably the tip portion comprises a relatively very small cylindrical shaft provided with a conical polishing end which is designed to permit access to the more difficult to reach areas of tooth anatomy. A preferred material for the tip portion is plastic made of a multiplicity of fibers axially aligned, adhesively coated and pressed together to form a cylindrical, unitary piece which exhibits good properties to apply polishing compositions to teeth and tooth restoration materials and sufficient strength in small diameter configuration for safe usage within the oral cavity at rotating speeds between about 1000 to 10,000 rpms.

12 Claims, 1 Drawing Sheet

ROTARY DENTAL ABRASIVE POLISHING APPLICATOR

TECHNICAL FIELD

The present invention relates generally to rotary polishing tools and particularly to rotary dental abrasive polishing tools to provide a mirror-like finish to tooth and tooth restoration materials.

BACKGROUND ART

There are several well-known rotary dental polishing applicator tools for applying abrasive polishing compositions to teeth and tooth restoration materials. Such tools include applicator tips such as rubber prophy cups, bristle prophy brushes, and felt or felt-like bobs and wheels. While many of these tools have been long used in dental laboratory practice to provide the final finish to tooth restoration materials, over the past several years, dentists have adopted "chair-side" techniques in their offices for fine polishing of tooth and tooth restoration materials within the patient's oral cavity.

While generally felt wheels and bristle brushes have been very popular for laboratory use, their size and configuration limits their applicability for some intra-oral applications. Similar limitations are true regarding the other prior types of polishing applicator tools which cannot effectively be used in the more difficult access areas such as interproximal spaces adjacent to the gingiva.

The material used for the polishing applicator tips has heretofore been of a relatively soft nature or is provided with an interrupted surface to which the polishing composition will tend to adhere and which will not damage or otherwise undesirably alter the finish of the tooth surface. However, these materials, while satisfactory in larger sizes and shapes for polishing the larger, exposed tooth surfaces, are not well-suited to a reduction in size which would permit effective, safe access to the more difficult to reach tooth surfaces.

As abrasive polishing techniques using diamond polishing compositions have moved into intra-oral applications, there has been an unsolved need to develop new methods and new applicator tips to more fully and effectively permit polishing of any area of the whole tooth surface to the desired mirror-like finish.

SUMMARY OF THE INVENTION

The present invention relates to a novel dental polishing applicator particularly adapted for use with conventional rotary dental handpieces. The polishing applicator of the present invention comprises a connector portion in the form of a cylindrical shaft adapted for conventional removable insertion into the rotary handpiece at one end and for removably receiving a polishing applicator tip portion at the opposing end.

The applicator tip portion comprises a one piece cylindrical shaft having an outer conical shaped end of relatively small dimensions to allow access to the more difficult to reach tooth surface areas, such as interproximal spaces and areas adjacent to the gingiva. The small dimensions of such a polishing applicator tool require the tip portion to be sufficiently strong to resist breakage yet have a surface capable of adequately functioning as an effective rotary polishing tool to maintain a sufficient amount of an abrasive polishing composition between the tool surface and the tooth surface during use.

In the preferred embodiment disclosed a material having these characteristics is a plastic material constructed of a plurality of small diameter fibers aligned parallel to their axis and adhesively coated and pressed together to form a strong, generally cylindrical shaft. Such a material has a microscopically porous surface resulting from trans-section of capillary pathways formed between the fibers. The resulting composite material may be machined to a configuration allowing access to the areas of the tooth heretofore not easily or safely reachable using the prior, conventional dental polishing applicators.

This composite material functions surprisingly well to maintain a sufficient amount of a dental diamond polishing composition in a functional relationship between the contacting surfaces during use to provide effective microscopic polishing results.

One end of the applicator tip is easily received in a removably fixed friction or interference fit in a socket provided in the connecting portion. The polishing end of the applicator may be ground to the desired configuration, such as a relatively small cone or the like. The conical shaped polishing end, when loaded with a small amount of dental diamond polishing composition, functions to polish teeth and tooth restoration materials to a very fine, mirror-like, finish when operatively connected and driven by a conventional dental rotary handpiece.

OBJECTS

Therefore it is a primary object of the present invention to provide a dental polishing applicator having a novel, single use, tip portion which possesses the reduced size and configuration allowing efficient and easier access to the more difficult to reach areas of tooth structure in the oral cavity.

It is another object of the present invention to provide an applicator tool of the type described which is made from a material which has the required good properties for fine polishing applications, but also possesses sufficient strength to be fashioned into the small dimensions and configurations necessary to access the difficult to reach tooth surfaces encountered in intra-oral dental applications.

It is a further object of the present invention to provide a novel method for polishing teeth in intra-oral applications using a material which comprises a multiplicity of parallel aligned fibers formed into a strong, relatively dense, cylindrical shape and which possesses a porous surface which functions surprisingly well as a dental polishing applicator to provide the desired mirror-like final finished surface.

Figures 1, 2:
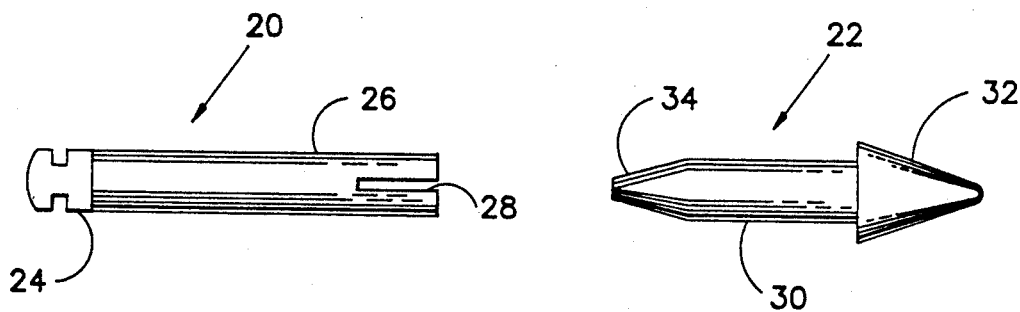
FIG. 1 is a side elevational view of the re-usable connecting means of a dental polishing applicator constructed in accordance with the present invention.
FIG. 2 is a side elevational view of the applicator tip portion of a dental polishing applicator constructed in accordance with the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other elements where such connection is recognized as being equivalent by those skilled in the art.

DETAILED DESCRIPTION

Figure 3:
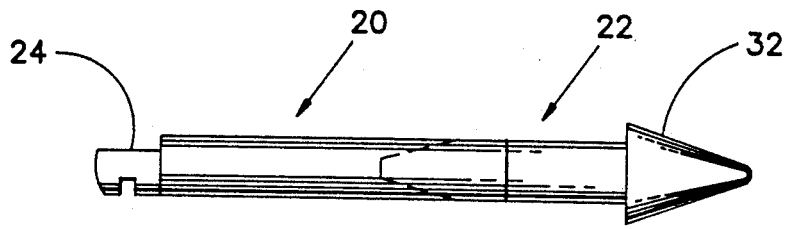
FIG. 3 is a side elevational view of the connecting means and tip portion shown in FIGS. 1 and 2 assembled together.

A dental polishing applicator tool mountable to a rotary dental handpiece and constructed in accordance with the present invention is shown in FIGS. 1-3. The polishing tool comprises a connecting portion 20 and a polishing applicator tip 22.

Connecting portion 20 includes a cylindrical shaft provided with a first end 24 having means for conventional releasably fixing into a rotary dental handpiece, such as the well-known latch type shown in FIGS. 1-3. The opposing outer end 26 is provided with a tubular socket portion preferably provided with opposing slots 28 for interfering, releasable engagement with one end of the polishing tip 22. Preferably connecting portion 20 is made of stainless steel and may be cleansed and reused.

End 24 provided with a groove and a milled flat that may be removably mounted into the standard, conventional rotary handpiece provided with a conventional latch type socket to removably receive the shaft of conventional rotary dental tools. Other conventional forms of connecting means, such as a screw type, friction-grip type or laboratory handpiece type could also be used depending upon the type of receiving socket of the dental handpiece without departing from the present invention.

The polishing applicator tip 22 includes an integrally formed cylindrical shaft 30 having a first end 32 provided with an enlarged conical configuration forming a polishing surface and an opposing tapered end 34. End 34 is configured to be easily received into the socket portion 26 of connecting means 20 to guide the adjacent untapered diameter portion of shaft 30 into a removable friction or interfering fit within socket portion 26. When fully seated within socket portion 26, polishing tip 22 is tightly gripped so as to rotate with connecting means 20 driven by a rotary handpiece 40, such as diagrammatically illustrated in FIG. 4. The slots 28 function as biased fingers allowing a slight expansion of the tubular socket, yet are biased to grip the shaft 30.

Upon development of suitable economical technology in machining or crush grinding suitable configurations of end 34 or the development of suitable receiving sockets on dental handpieces, the connecting collet type portion such as 20 may be eliminated and the applicator tip portion 22 would be connected directly to the handpiece.

The polishing end 32 of polishing applicator tip 2 has relatively small dimensions compared to conventional abrasive polishing dental applicators and is adapted to provide access to those more difficult to reach areas of a tooth surface, such as between the interproximal spaces adjacent to the gingiva and sub-gingival surfaces.

The preferred shape of polishing end 32 is a generally conical configuration and provides the most generally useful shape. However, other well-known shapes such as found in dental burs may be useful for particular applications.

Preferably, the largest diameter of the base of the conical end 32 is about 2 to 4 mm with the tapered surface extending to the outer tip being about 4 to 5 mm. The shaft portion 30 has an outer diameter approximately a few thousands larger than the typical internal diameter of the socket portion of connecting means 20, which itself is closely similar to the diameter of the shafts of most conventional dental burs presently in common use. A diameter of about 0.08 inches provides very adequate strength for the main portion of shaft 30.

Figure 4:
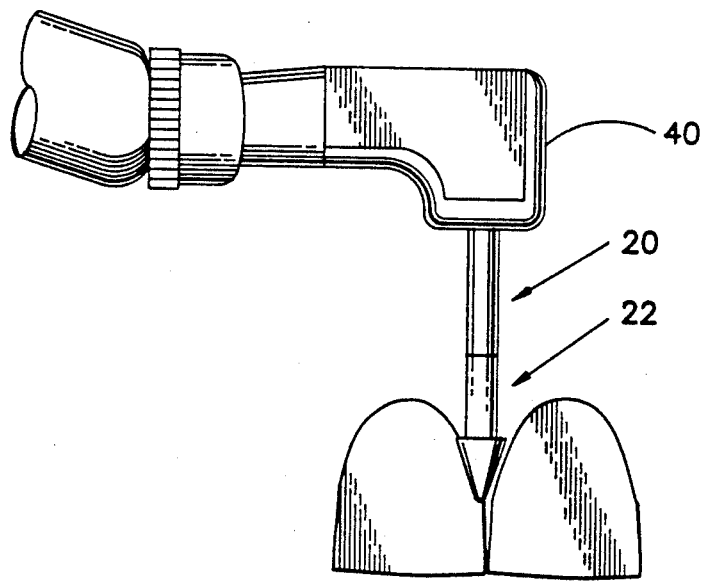
FIG. 4 is a side elevational view of the dental polishing applicator shown in the preceding figures inserted into a representation of a rotary dental handpiece for use with a diagrammatic illustration of adjacent teeth.

As diagrammatically illustrated in FIG. 4, the polishing end 32 of applicator 20 is conformed to allow efficient and effective access to the tooth areas which conventional polishing applicators cannot effectively or safely reach.

However, given the relatively small size necessary to accomplish this function and the requirements of functioning as an effective rotary dental abrasive polishing applicator, the type of material which can be used to effectively accomplish the intended purpose is limited. The material must be sufficiently strong so as not to break, splinter or chip under the relatively rigorous polishing conditions, and particularly to be safe for intra-oral use. Further, the surface of the material must be suitable to adequately accept a dental abrasive polishing composition and effectively provide the desired polishing action in the rotating contact with the working surface. Therefore it should have a microscopically porous or otherwise interrupted surface to permit a sufficient amount of the polishing composition to be effectively carried between the rotating applicator and the work surface and yet not so rough as to tend to break through the film of the polishing composition and directly contact the tooth surface. Further, the surface hardness or compressibility of the material should be within a range which promotes efficient polishing action in forcing the abrasive polishing composition against the tooth surface under the typical and recommended loading pressures for dental polishing procedures. Preferably, at least some reasonable degree of elastic deformation of the polishing end 32 relative to the tooth surface occurs during normal use to promote efficient polishing action without discomfort to the patient.

A preferred material which has surprisingly effective properties in performing this polishing action and which has superior strength at the small size required, is a plastic material formed by a multiplicity of parallel disposed, small diameter, plastic fibers aligned parallel to their axis and coated with a suitable adhesive and pressed together to form a bonded unitary cylindrical rod-like member. Upon appropriate curing of the adhesive, this cylindrical member can be conventionally machined to form different configurations such as the shaft 30 having the integrally formed larger conical end 32 and tapered end 34. It possesses a porous surface having a capillary type fluid transfer capability.

Such a material has been priorly used primarily as a tip for writing instruments such as used in the well-known highlighter markers and the like, as well as other capillary type fluid transfer applications. These materials are presently commercially available from American Filtrona Company of Richmond, Va.

Many types of synthetic plastic fibers are used in this composite form and are commercially available, such as nylon, polyester, acrylic, olefin and aramids. A preferred material for use in the present invention is nylon. However, certain natural fibers or animal hair may also be expected to be a suitable replacement for synthetic fibers to form such a composite material. Appropriate selection of such fibers and bonding material to assure adequate strength and a suitable hardness to provide an appropriate surface would be required to function in dental polishing applications in a similar manner as the synthetic fiber composition material presently available.

Such a product in the preferred nylon material as referred to above provides sufficient strength and a microscopically porous surface which surprisingly functions very well to effectively polish tooth and tooth restoration materials when used with diamond containing dental polishing compositions useful in providing a very fine, smooth, mirror-like finish.

Dental polishing applicator tips of this nylon fiber construction also are relatively inexpensive in volume and therefore may be economically employed in the desirable single use, disposable form.

The small size required to enable the user to effectively reach the more difficult to access areas of the tooth surface can not be effectively accessed using the typical, conventional forms of dental polishing applicators. These conventional applicators include felt bobs and wheels, bristle brushes and rubber prophy cups. While these conventional applicators are effective for polishing the larger more accessible tooth areas, they are not readily and economically formed in an effectively small configuration useful to reach the interproximal spaces and sub-gingival areas.

In operation, the user inserts end 34 of a polishing applicator 22 into the socket end 26 of connecting means 20. The opposing end 24 of connecting means 20 is removably inserted into an appropriate socket of a conventional low speed dental handpiece, such as 40. A small amount of a dental diamond polishing composition is applied to the enlarged polishing end 32 of the polishing tip 22.

Then the polishing end 32 is positioned adjacent to the tooth surface in the patient's mouth. The handpiece is then adjusted to the desired rotary speed. Typically this speed could be in the range of about 1000 to 10,000 rpm, however, the preferred range is about 5000 to 7000 rpm for most fine finishing applications.

Tests using the applicator of the present invention have shown that a tool having relatively very small dimensions and a relatively hard, yet porous surface accepts the diamond dental compositions very well to provide very effective polishing action at conventional speeds of rotation typically employed in such fine finishing procedures. The preferred size and configuration such as shown in FIG. 2 of the applicator tip has been used in tests between the interproximal spaces adjacent to the gingiva and shown to be effective to provide a very smooth surface.

Examples of diamond polishings commonly used in fine finishing dental applications include those commercially available in paste form containing 1 to 5 micron sized diamond particles. However, a preferred polishing composition containing diamond particles ranging from about one-quarter to nine micron size diamonds in a semi-gel or sol carrier is disclosed in applicant's copending patent application, Ser. No. 07/611,991, filed Nov. 9, 1990. This preferred polishing composition appears to work best with an applicator tip such as disclosed herein and adheres very well to the small, porous surface of the polishing end 32 during use.

While other materials may be expected to be useful for the polishing applicator tip 32 as disclosed herein, such materials must have sufficient strength to be safe for use in intra-oral applications. Additionally, a porous or otherwise equally effective surface permitting the polishing composition to remain on the polishing tip during use is required to provide effective polishing action on the tooth surface. Assuming the larger, easily reached areas have been polished using conventional polishing applicators, the polishing tool of the present invention can be conveniently used to safely and more fully provide the whole tooth surface with a smooth mirror-like finish to improve the desired aesthetic appearance. Further the removal of the microscopic scratches left by prior tooth contouring and finishing treatments also reduces the areas in which plaque tends to form, thereby enhancing the therapeutic benefits provided by fine finishing and polishing techniques.

It should also be noted that the applicator tip portion could be made to conform at its inner end 30 to directly be inserted into a rotary handpiece if the handpiece is adapted to suitably frictionally grip the shaft portion 22. In such a modification, the connecting means 20 would not be necessary.

While certain preferred embodiments of the present invention have been disclosed in detail, it is to be understood that various modifications may be adopted without departing from the spirit of the invention or scope of the following claims.

We claim:

1. A polishing tool for power rotary dental handpieces to apply an abrasive polishing composition to teeth and tooth restoration materials comprising, in combination;
   a) a generally cylindrical connecting portion having one end conformed for releasably fixed connection to said rotary dental handpiece and an opposing end provided with a tubular socket portion;
   b) a polishing applicator tip removably inserted into said socket portion and including an integrally formed cylindrical shaft having a first polishing end portion and an opposing second end portion tapered sufficiently to be slideably received and releasably fixed within said tubular socket portion of said connecting portion collet; said applicator polishing tip comprising a plurality of fibers taken from a group consisting of natural or synthetic materials, said fibers aligned in parallel relationship and bonded to one another along their axial length to form said cylindrical shaft and said polishing end portion, at least said polishing end portion having a microscopically porous surface.

2. The tool defined in claim 1 wherein said tubular socket portion is provided with a plurality of axial slits forming fingers to biasly grip the shaft portion of said polishing tip.

3. The tool defined in claim 1 wherein said fibers comprises a plastic material.

4. The tool defined in claim 3 wherein said fibers are nylon.

5. The tool defined in claim 1 wherein said polishing end has a generally conical configuration provided with a base having a diameter larger than the diameter of said shaft portion.

6. A polishing applicator tool for power rotary dental handpieces for application of an abrasive polishing composition containing non-fixed abrasive particles to teeth and tooth restoration materials comprising;
   a) an integrally formed, one piece cylindrical shaft having a first polishing end portion for carrying said polishing compound and an opposing end portion conformed for cooperative demountable attachment to said rotary dental handpiece for rotation about the axis of said shaft, said shaft and said polishing end portion being formed of a plurality of fibers having a hardness value less than the materials to be polished and aligned in parallel relationship along their axial length and adhesively bound together, said polishing end being ground to a predetermined generally conical configuration including a microscopically porous surface configured to retain said polishing compound in operative relationship between said porous surface and the tooth materials being polished.

7. The polishing applicator defined in claim 6 wherein said fibers comprise a synthetic material.

8. The polishing applicator defined in claim 7 wherein said synthetic material is a plastic material.

9. The polishing applicator defined in claim 8 wherein said plastic material is nylon.

10. A method for abrasively polishing the surface of teeth and tooth restoration materials comprising forcing a diamond containing polishing composition against the surface of the tooth or tooth restoration material with an applicator having an outwardly extending polishing tip integrally formed in one piece on a generally cylindrical shaft portion with the opposing end of said shaft portion removably mounted to a rotary dental handpiece, while maintaining a rotational speed of said applicator relative to said surface of the tooth or tooth restoration material above about 1000 revolutions per minute and a loading pressure sufficient to remove materials from the surface of said tooth or tooth restoration material; said shaft and said polishing tip comprising a synthetic material formed from a multiplicity of elongated fibers aligned in parallel relationship to one another and adhesively fixed together in along their axial length and said polishing tip having a porous surface and an inherent capillary-type fluid transfer capability.

11. The method defined in claim 10 wherein said polishing tip has a conical configuration having its largest diameter no greater than about 2 to 4 mm.

12. A polishing applicator tool for power rotary dental handpieces to apply a polishing composition containing non-fixed abrasive particles into polishing engagement with teeth and tooth restoration materials comprising, in combination;
   a) a generally cylindrical connecting portion having one end conformed for releasably fixed connection to said rotary dental handpiece for rotation about the axis thereof and an opposing end provided with a tubular socket portion;
   b) a polishing applicator tip removably inserted into said socket portion including a one piece integrally formed cylindrical shaft having a first polishing end portion for receiving said polishing composition and an opposing second end portion conformed to be disposed in a removably fixed relationship to said tubular socket for rotation with said connecting portion, said shaft being formed of a plurality of fibers having a hardness value less than the tooth materials being polished and aligned in parallel relationship to the axis of rotation of said shaft and adhesively bound together, said polishing end portion being ground to a predetermined configuration and including a microscopically porous surface configured to retain said polishing composition in operative polishing relationship upon rotational engagement with said materials being polished.

* * * * *